United States Patent [19]
Rother et al.

[11] Patent Number: 5,562,904
[45] Date of Patent: Oct. 8, 1996

[54] RETROVIRAL TRANSDUCTION OF CELLS USING SOLUBLE COMPLEMENT INHIBITORS

[75] Inventors: Russell P. Rother, Cheshire; Scott A. Rollins, Monroe; James M. Mason, Wallingford; Stephen P. Squinto, Bethany, all of Conn.

[73] Assignee: Alexion Pharmaceuticals, Inc., New Haven, Conn.

[21] Appl. No.: 278,550

[22] Filed: Jul. 21, 1994

[51] Int. Cl.$^6$ .................................................. B61K 39/395
[52] U.S. Cl. .................................. 424/145.1; 424/130.1; 424/141.1; 514/44
[58] Field of Search .............................. 424/130.1, 141.1, 424/145.1; 514/44

[56] References Cited

PUBLICATIONS

Anderson, W. F., *Human Gene Therapy* 5:281–282, 1994.
Liszewski et al., "The Complement System," in *Fundamental Immunology* 3rd Ed., Paul, W. E., Ed. Raven Press, New York, 1993.
Takeuchi et al., *J. Virology* 68(12):8001–8007, Dec. 1994.
Albrecht et al., "*Herpesvirus saimiri* has a gene specifying a homologue of the cellular membrane glycoprotein CD59" *Virology*, 190:527–530, 1992.
Albrecht and Fleckenstein, "New member of the multigene family of complement control proteins in *Herpesvirus saimiri*" *J Virology*, 66:3937–3940, 1992.
Bartholomew et al., "Lysis of oncornaviruses by human serum" *J Exp Med*, 147:844–853, 1978.
Bartholomew and Esser, "Mechanism of antibody–independent activation of the first component of complement (C1) on retrovirus membranes" *Biochem*, 19:2847–2853, 1980.
Cooper et al., "Lysis of RNA tumor viruses by human serum: Direct antibody–independent triggering of the classical complement pathway" *J Exp Med*, 144:970–984, 1976.
Culver et al., "In vivo gene transfer with retroviral vector–producer cells for treatment of experimental brain tumors" *Science*, 256:1550–1552, 1992.
Galili et al., "Evolutionary relationship between the natural anti–Gal antibody and the Galα1→3 Gal epitope in primates" *Proc Natl Acad Sci, USA*, 84:1369–1373, 1987.
Isaacs et al., "Vaccinia virus complement–control protein prevents antibody–dependent complement–enhanced neutralization of infectivity and contributes to virulence" *Proc Natl Acad Sci, USA*, 89:628–632, 1992.

McNearney et al., "Herpes simplex virus glycoproteins gC–1 and gC–2 bind to the third component of complement and provide protection against complement–mediated neutralization of viral infectivity" *J Exp Med*, 166:1525–1535, 1987.
Neethling et al., "Protection of pig kidney (PK15) cells from the cytotoxic effect of anti–pig antibodies by α–galactosyl oligosaccharides" *Transplantation*, 57:959–963, 1994.
Ram et al., "Toxicity studies of retroviral–mediated gene transfer for the treatment of brain tumors" *J Neurosurg*, 79:400–407, 1993.
Repik et al., "Differential host–dependent expression of α–galactosyl epitopes on viral glycoproteins: a study of eastern equine encephalitis virus as a model" *J Gen Virol*, 75:1177–1181, 1994.
Rother et al., "Inhibition of complement–mediated cytolysis by the terminal complement inhibitor of herpesvirus saimiri" *J Virol*, 68:730–737, 1994.

Welsh et al., "Human serum lyses RNA tumour viruses" *Nature*, 257:612–614, 1975.

Welsh et al., "Inactivation and lysis of oncornaviruses by human serum" *Virology*, 74:432–440, 1976.

Widner and Brundin, "Immunological aspects of grafting in the mammalian central nervous system. A review and speculative synthesis", *Brain Res Rev*, 13:287–324, 1988.

Immunology, vol. 76, 1992, Rooney et al., "Characterization of the membrane attack complex inhibitory protein CD59 antigen on human amniotic cells and in amniotic fluid" pp. 541–547.

The Journal Of Immunology, vol. 151, 1993, Lehto et al., "Interactions of soluble CD59 with the terminal complement complexes" pp. 4941–4949.

*Primary Examiner*—Robert D. Budens
*Attorney, Agent, or Firm*—Seth A. Fidel, Ph.D.; Maurice M. Klee, Ph.D.

[57] ABSTRACT

Methods and compositions are provided for facilitating gene therapy procedures involving the transduction of target cells with retroviral vector particles in the presence of complement containing body fluids. The administration of soluble complement inhibitor molecules to body fluids prevents the complement mediated inactivation of the retroviral vector particles, and provides a safety mechanism for such gene therapy procedures, as the action of soluble complement inhibitors is transient, and any retroviral vector particles present after the return of uninhibited complement activity will be inactivated. Preferred soluble complement inhibitors for use in the practice of the present invention include complement inhibitory anti-complement component mAbs (including complement inhibitory anti C5 antibodies).

5 Claims, 5 Drawing Sheets

RETROVIRAL TRANSDUCTION OF CELLS USING SOLUBLE COMPLEMENT INHIBITORS

FIELD OF THE INVENTION

The present invention relates to gene therapy mediated by the transduction of primate cells by retroviral vector particles (RWPs) and, in particular, to the modulation of complement activity to allow the medical use of such particles for transduction of human and other primate cells without removing the cells from contact with the extracellular fluids of the host organism.

BACKGROUND OF THE INVENTION

I. Retroviruses

The Retroviridae virus family encompasses all viruses containing an RNA genome and producing an RNA-dependent DNA polymerase (reverse transcriptase). In broadest overview, the life cycle of a retrovirus comprises entry of an infectious retroviral particle into a host cell, integration of the virus' genetic information into the host cell's genome, and production of new infectious retroviral particles by the biosynthetic machinery of the infected host cell. More specifically, upon entering a cell, a retroviral particle initiates a series of interactive biochemical steps that result in the production of a DNA copy of the virus' RNA genome and its integration into the nuclear DNA of the cell. This integrated DNA copy is referred to as a provirus and can be inherited by any daughter cells of the infected cell like any other gene. Genes contained within the integrated provirus may be expressed in the host cell.

All retroviral particles share common morphological, biochemical, and physical properties, including:

(1) A linear, positive-sense, single-stranded RNA genome composed of two identical subunits and making up about 1% of the mass of the virus.

(2) At least three types of proteins encoded by the viral genome, i.e., gag proteins (the group antigen internal structural proteins), pol proteins (the RNA-dependent DNA polymerase and integrase proteins), and env proteins (the viral envelope protein or proteins). These proteins together make up about 60%–70% of the mass of the virus.

(3) Lipid derived from the cell membrane of an infected cell making up about 30%–40% of the mass of the virus.

(4) Carbohydrate associated with the env proteins, making up about 2–4% of the mass of the virus.

(5) An overall spherical morphology with variable surface projections.

(6) An isocahedral capsid structure containing a ribonucleoprotein complex within an internal nucleoid or nucleocapsid shell.

In addition to genes encoding the gag, pol, and env proteins, the genome of the retrovirus includes two long terminal repeat (LTR) sequences, one at each end of the linear genome. These 5' and 3' LTRs serve to promote transcription and polyadenylation of viral mRNAs. Adjacent to the 5' LTR are sequences necessary for reverse transcription of the viral genome (the tRNA primer binding site) and for efficient encapsulation of viral RNA into particles (the Psi site). Other genes may also be found between the 5' and 3' LTRs of the retroviral genome.

If heterologous genes are inserted in between the 5' and 3' LTRs of a retroviral genome, which is then packaged into a functional retroviral particle, the resulting recombinant retroviral particle is capable of carrying the heterologous genes into a host cell. Upon integration of the recombinant retroviral genome into the host cell's genome as part of the proviral DNA, the heterologous genes may be expressed.

These properties and capabilities have led to the development of retroviral vectors, retroviral packaging and producer cells, and retroviral vector particles (collectively referred to as retroviral transduction systems) as efficient means of stably introducing exogenous genes of interest into mammalian cells. Certain retroviruses have been engineered to produce non-infectious retroviral transduction systems that are especially useful in the field of gene therapy. See Anderson, 1992; Miller, 1992; Mulligan, 1983; Mann, 1983; Cone and Mulligan, 1984.

II. Gene Transfer by Retroviral Transduction

Retroviral transduction systems of the type discussed above are able to introduce recombinant nucleic acid molecules into mammalian target cells, and to efficiently integrate DNA molecules containing some or all of the genetic information (sequence) of the introduced recombinant nucleic acid molecule into the genome of the target cell so that the introduced genetic material is replicated and is stably and functionally maintained (and any encoded gene products are expressed) in the cell without the danger of the production of replicating infectious virus. See, for example, Ausubel, et al., Volume 1, Section III (units 9.10.1–9.14.3), 1992.

Retroviral vector particles are particularly useful for genetically modifying mammalian cells, including human cells, because the efficiency with which they can transduce target cells and integrate their genetic information into the target cell genome is higher than that achievable using other systems of introducing exogenous genetic material into cells. Other advantages associated with the use of retroviral vector particles as gene therapy agents include stable expression of transferred genes, capacity to transfer large genes, and lack of cellular cytotoxicity. Additionally, retroviral vector particles may be constructed so as to be capable of transducing mammalian cells from a wide variety of species and tissues.

Successful gene transfer by transduction with a retroviral vector particle (RWP) requires: 1) incorporation of a gene of interest into a retroviral vector; 2) packaging of a vector-derived viral genome into a RVVP; 3) binding of the RWP to the target cell; 4) penetration of at least the RNA molecules comprising the viral genome into the target cell (generally associated with penetration of the RVVP and uncoating of the RVVP); 5) reverse transcription of the viral RNA into pre-proviral cDNA; 6) incorporation of the pre-proviral cDNA into preintegration complexes, 7) translocation of the preintegration complexes into the target cell nucleus, 8) generation of stable proviral DNA by integration of the pre-proviral cDNA into the host genome (typically mediated by the viral integrase protein); and 9) expression of the gene of interest. In the in vivo setting (and in some ex vivo settings), the RVVP must survive in the extracellular fluids of the host organism in an active state for a period sufficient to allow binding and penetration of the host target cell by the RVVP.

Gene Therapy

There is active research, including clinical trial research, on treatment of disease by introduction of genetic material into some of the cells of a patient. A variety of diseases may be treated by therapeutic approaches that involve stably introducing a gene into a cell such that the gene may be transcribed and the gene product may be produced in the cell. Diseases amenable to treatment by this approach include inherited diseases, particularly those diseases that are caused by a single gene defect. Many other types of diseases, including acquired diseases, may also be amenable to gene therapy. Examples of such acquired diseases include many forms of cancer, lung disease, liver disease, and blood cell disorders. See Anderson, 1992; Miller, 1992; and Mulligan, 1993.

Delivery of the gene or genetic material into the cell is the first critical step in gene therapy treatment of disease. A variety of methods have been used experimentally to deliver genetic material into cells. Most research has focused on the use of retroviral and adenoviral vectors for gene delivery. As discussed above, RVVPS are particularly attractive because they have the ability to stably integrate transferred gene sequences into the chromosomal DNA of the target cell and are very efficient in stably transducing a high percentage of target cells. Accordingly most clinical protocols for gene therapy use retroviral vectors (see, for example, Miller, 1992; and Anderson, 1992).

Most gene therapy protocols involve treating target cells from the patient ex vivo and then reintroducing the cells into the patient. Patients suffering from several inherited diseases that are each caused by a single gene defect have already received gene therapy treatments. Such treatments generally involve the transduction of the patient's cells in vitro using RVVPs designed to direct the expression of therapeutic molecules, followed by reintroduction of the transduced cells into the patient. In many cases such treatments have provided beneficial therapeutic effects.

For many diseases, however, it will be necessary to introduce the gene into the target cell in situ, because the target cells cannot be removed from and returned to the body. In other cases, cells that are removed from the patient must be maintained in the presence of body fluids until being returned to the body. Stem cells, particularly hematopoietic stem cells, are an especially important type of target cell for gene therapy of inheritable and acquired blood disorders. Such cells are intrinsically unstable in vitro, and tend to differentiate into cells that are less attractive targets for gene therapy, especially when they have been washed free of the fluids that surround them in vivo and transferred into body-fluid-free tissue culture media or the like.

Accordingly, it is desirable to transduce stem cells as quickly as possible, and ex vivo treatment of such cells with RVVPs is best carried out in the cells natural milieu, i.e., in cells that have not been washed or otherwise removed from the body fluids in which they are obtained, e.g., hematopoietic stem cells in bone marrow aspirates. In the case of stem cells in bone marrow, current medical procedures for bone marrow transplant involve mixing an ex vivo bone marrow aspirate (which is inevitably obtained as a mixture of bone marrow and blood) with heparin and tissue culture medium. The condition of such cells, that have been removed from the body but kept in diluted or undiluted fluids of their natural milieu, is referred to hereinafter as the "ex vivo unwashed state".

III. Complement and Retroviral Vector Particles

A longstanding problem associated with the use of RVVPs as gene therapy vectors in cells in vivo or in cells in the ex vivo unwashed state relates to the inactivation of many retroviruses (and RVVPs derived therefrom) by the body fluids (e.g., blood, bone marrow, lymph) of many primates, including Old World monkeys, apes, and humans. Indeed, it has been known for almost two decades that certain retroviruses are rapidly inactivated in human serum (Welsh et al., 1975), as well as serum from nonhuman primates (Welsh et al., 1976). This problem has precluded the use of such RVVPs for gene therapy in vivo or in the ex vivo unwashed state.

The complement system has long been implicated in the serum mediated inactivation of retroviruses, as serum deficient in C2, C4 or C8 does not cause the detectable release of reverse transcriptase from retroviral virions (Welsh et al., 1975; Cooper, et al., 1976). The protection of active retroviral particles from human complement is thus necessary for the use of the RVVPs to mediate gene therapy in human cells in vivo or in the ex vivo unwashed state. Accordingly, to date, gene transfer by retroviral transduction has been, for the most part, limited to cells that were removed from the extracellular fluids of the host organism (i.e., ex vivo cells that are not in the ex vivo unwashed state) and thus were not subjected to complement attack. This limitation has represented a significant shortcoming of this technology.

The need for methods allowing transduction of primate cells in situ, in vivo, or in the ex vivo unwashed state has resulted in the development of methods designed to prevent the inactivation of retroviruses by human and other primate sera. Such methods have included the removal of cells from the extracellular fluids of the host organism, as discussed above, as well as the masking of virion structures that can activate complement activity by administration of isolated $C1s$ and/or $C1q$ complement subcomponents, as discussed below under the subheading "The Direct C1 Binding Mechanism".

Significantly, with regard to the present invention, no previous methods for allowing transduction of primate cells in situ, in vivo, or in the ex vivo unwashed state have included the administration of soluble complement inhibitors.

The Direct C1 Binding Mechanism

Retroviruses that are sensitive to human serum can activate the human classical complement pathway by a mechanism that involves a unique, antibody independent process. This process is found in many primates and is generally not present in other mammals (see Cooper, et al., 1976). This mechanism is activated when complement component C1 binds to retroviral virions directly and triggers the classical complement pathway, just as the pathway is normally activated by an antigen-antibody complex (Bartholomew, et al., 1978). The complement cascade then causes the eventual destruction and elimination of the virus.

Complement component C1 is a large complex protein composed of 3 subunits designated $C1q$, $C1s$, and $C1r$. $C1q$ is itself composed of 18 polypeptide chains of three different types designated A, B, and C. Six molecules each of chains A, B, and C compose the $C1q$ subunit. There are two molecules each of the $C1s$ subunit and the $C1r$ subunit that associate with $C1q$ to form the C1 complement component. The $C1q$ subunit contains multiple identical binding sites for the complement binding regions of immunoglobulin molecules, which regions are only exposed upon the formation of an antigen antibody complex. In the classical pathway, the binding of $C1q$ to these regions of antigen-bound antibody molecules causes a conformational change in the C1 complex resulting in the enzymatic activation of C1 to yield an active serine protease. The C1s and C1q subunits both have a molecular weight of approximately 85 kDa, and each is cleaved to smaller molecular weight forms of approximately 57 kDa and 28 kDa during activation of the C1 complex. The 57 kDa forms of C1s and C1q present in the activated C1 complex contain the protease activity.

In the activation of the classical complement pathway by retroviruses via the direct binding of C1, the C1q subunit of C1 binds directly to at least one site on the retroviral virion. In the case of Moloney murine leukemia virus, the p15E viral protein has been identified as the C1 binding receptor. See Bartholomew, et al., 1978. In contrast to the antibody-mediated classical complement pathway, binding by both the C1q subunit and the C1s subunit of the C1 complex is required for complement activation by retroviral particles via this mechanism. Furthermore, the C1*s* subunit and C1*q* subunit must bind the viral particle when they are present in a functional C1 complex in order for complement activation to occur by this mechanism. See Bartholomew, et al., 1980.

The C1*s* subunit is also believed to have a specific binding site for retroviral envelope proteins. It has been shown, using inactive retrovirus, that prebinding with C1*s* blocks the subsequent activation of the complement cascade by the retrovirus in vitro. See Bartholomew, et al., 1980.

Co-pending U.S. patent application Ser. No. 08/098,944 ("the '944 application"), filed Jul. 28, 1993 in the name of James M. Mason and entitled "Pre-binding of Retroviral Vector Particles with Complement Components to Enable The Performance of Human Gene Therapy In Vivo," discuses the use of free C1*q* or free C1*s* to block the subsequent binding and/or activation of the C1 complex by active retrovirus particles including RVVPs.

As described therein, C1*s* or C1*q* or a combination thereof are incubated with the RVVPs in vitro to form complexes with the particles. This complex formation blocks the binding sites for C1*s* and/or C1*q* and thereby protects the particles from subsequent inactivation or lysis when the RVVPs are exposed to complement. As further described therein, blockade of intact C1 binding to RVVPs can be achieved by the use of fragments of antibodies that bind the viral envelope proteins of RVVPs but lack complement binding regions.

As disclosed in the '944 application, the use of these methods improves the survival of RVVPs in human serum, but does not completely inhibit retroviral inactivation. The reasons for the incomplete nature of the inhibition of retroviral inactivation by these methods have heretofore been unknown, but are now believed to be due in part to the presence of additional RVVP-associated factors, other than the C1 binding factors discussed above, that can bind to antibodies in Old World primate and human blood and thereby activate the complement system. In accordance with copending U.S. patent application Ser. No. 08/278,639, entitled "Retroviral Transduction of Cells in the Presence of Complement", which is being filed concurrently herewith in the names of Russell P. Rother, Scott A. Rollins, William L. Fodor, and Stephen P. Squinto, now abandoned, these factors are present in the form of alpha galactosyl epitopes found as part of retroviral membrane glycoproteins.

Many gene therapy methods require very high titers of transducing RVVPs in order to be practiced effectively. The methods of the '944 application do not completely inhibit complement mediated RVVP inactivation, and thus may not provide high enough titers of RVVPs in vivo or in the ex vivo unwashed state for the effective practice of all such gene therapy methods in these settings.

Thus, a need continues to exist for methods to control complement-mediated destruction of RVVPs. The present invention provides new methods and compositions that can be used in conjunction with, or as an alternative to other methods of protecting RVVPs from inactivation by complement such as the blockade of intact C1 binding to RVVPs as disclosed in the '944 application. The methods of the present invention thus allow the practice of more efficient gene therapy procedures in vivo and in the ex vivo unwashed state.

Although the C1*q* and C1*s* polypeptides and antibody fragments used in the practice of the invention of the '944 application act to inhibit the activation of the complement cascade, these polypeptides are not considered no be complement inhibitor molecules, as they do not interact with complement components, but rather act by masking a target viral protein, thereby preventing the activation of complement component C1 by the viral protein. This masking of the target protein occurs without any direct or indirect interactions with any native complement components, and without alterations of the activities of native complement components, which interactions and alterations are associated with the actions of complement inhibitor molecules.

Along these same lines, copending U.S. patent application Ser. No. 08/278,639, entitled "Retroviral Transduction of Cells in the Presence of Complement", which is being filed concurrently herewith in the names of Russell P. Rother, Scott A. Rollins, William L. Fodor, and Stephen P. Squinto, now abandoned, discusses the use of certain galactosyl sugars to block the binding of certain preformed natural antibodies to RWPs. Such blockade of antibody binding can block the activation of the complement system by antigen-bound antibodies, and can thus reduce the inactivation of RVVPs by complement. If desired, these methods of using such sugars as well as other methods discussed in the above-referenced application can be used in conjunction with the methods of the present invention to effect even greater reductions of the inactivation of RVVPs by complement. Similarly to the case of the use of C1*q* and/or C1*s* discussed above, the blockade of antibody binding upon administration of the galactosyl sugars occurs without any direct or indirect interactions with any native complement components, and without alterations of the activities of any native complement components, which interactions and alterations are associated with the actions of complement inhibitor molecules.

Thus, as used herein, the term "complement inhibitor molecule" refers to any molecule that inhibits complement activity by interacting, either directly or indirectly, with a native complement component or cofactor so as to reduce complement activity, but not to molecules that interfere with complement activation only by masking structures of non-complement components (such as pathogen structures, e.g., retroviral envelope proteins, or antigen-bound antibodies), and not to molecules that interfere with antibody-antigen binding events that can serve to initiate complement activation. As discussed below, numerous molecules are known in the art that act to reduce complement activity, for example, by binding directly to complement components, or by sequestering cofactors such as divalent cations necessary for complement component activity. In accordance with the foregoing discussion, such molecules are referred to herein as complement inhibitor molecules.

IV. The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins (which are also found in most other body fluids, such as lymph, bone marrow, and cerebrospinal fluid) make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lyric functions.

The complement cascade progresses via the classical pathway or the alternative pathway. These pathways share many components, and, while they differ in their early steps, both converge and share the same terminal complement components responsible for the destruction of target cells and viruses.

The classical complement pathway is typically initiated by antibody recognition of and binding to an antigenic site on a target cell. This surface bound antibody subsequently reacts with the first component of complement, C1, which, as discussed above, includes subunits C1$s$, C1$r$, and C1$q$.

The C1$q$ subunit of C1 mediates the binding of C1 both to antigen-antibody complexes and to retroviruses, although, in the case of direct binding to retroviruses, the C1$s$ subunit also has a binding function. The bound C1 undergoes a set of autocatalytic reactions that result in the activation of the C1$r$ subunits, which in turn proteolytically activate the C1$s$ subunits, altering the conformation of C1 so that the active C1$s$ subunits are exposed on the exterior of C1, where they can interact proteolytically with complement components C2 and C4.

C1$s$ cleaves C2 and C4 into C2$a$, C2$b$, C4$a$, and C4$b$. The function of C2$b$ is poorly understood. C2$a$ and C4$b$ combine to form the C4$b$,2$a$ complex, which is an active protease known as the C3 convertase. C4$b$,2$a$ acts to cleave C3 into C3$a$ and C3$b$. C3$a$ is a relatively weak anaphylatoxin. C4$a$ is a stronger anaphylatoxin, and can induce degranulation of mast cells, resulting in the release of histamine and other mediators of inflammation.

C3$b$ has multiple functions. As opsonin, it binds to bacteria, viruses and other cells and particles and tags them for removal from the circulation. C3$b$ can also form a complex with C4$b$,C2$a$ to produce C4$b$,2$a$,3$b$, or C5 convertase, which cleaves C5 into C5$a$ (another anaphylatoxin), and C5$b$. C5$b$ combines with C6 yielding C5$b$,6, and this complex combines with C7 to form the ternary complex C5$b$,6,7. The C5$b$,6,7 complex binds C8 at the surface of a cell membrane. Upon binding of C9, the complete membrane attack complex (MAC) is formed (C5$b$–9) which mediates the lysis of foreign cells, microorganisms, and viruses.

A more complete discussion of the classical complement pathway, as well as a detailed description of the alternative pathway of complement activation, which pathway has also been implicated in the inactivation of RVVPs by human complement, can be found in Roitt, et al., 1988.

V. Inhibitors of the Complement System

Under normal conditions, homeostatic regulation of the actions of complement proteins is mediated by specific endogenous complement inhibitor molecules (CIMs), that can be found on the surfaces of most human cells. A number of endogenous CIMs have been identified that serve to protect cells from damage mediated by complement from concordant species. Pathogenic organisms and viruses are also known to produce CIMs (referred to hereinafter as "microbial CIMs") that are believed to allow the pathogens to evade destruction by the complement of their host organisms, and thus act to increase their virulence. Examples of these various types of complement inhibitor molecules are discussed below.

Endogenous CIMs

An inhibitor referred to as CD59 (also known as "MACIF," "protectin," or "p18"), acts to block the final step in the complement cascade leading to the assemblage of the lyric C5$b$–9 MAC. The complement inhibitory action of CD59 is greatest when the CD59 molecule is attached to the surface of a cell membranes but complement inhibitory activity of soluble forms of CD59 has also been reported. See Rooney and Morgan, 1992 and Lehto and Meri, 1993. A number of viral and non-human primate complement inhibitor proteins that are similar in structure and function to CD59 have been described (see copending U.S. patent application Ser. No. 08/105,735, filed Aug. 11, 1993, and copending PCT patent application Ser. No. PCT/US93/00672, filed Jan. 12, 1993).

Vitronectin (S-protein) is another terminal complement inhibitor protein. A serum glycoprotein found in plasma both in native and in partially proteolyzed form, it inhibits the lyric activity of the membrane attack complex of complement, by binding to nascent C5$b$–7 complexes, rendering them unable to bind to C8 and C9 (Tschopp, et al., 1988).

CD55, also known as decay accelerating factor (DAF) exerts its complement inhibitory effects on the actions of the C3 and C5 convertases. CD55 is a cell surface protein present on all cells including red blood cells. The action of CD55 prevents C3$b$ from reacting with other complement components, thus countervening complement mediated cytolysis. Both membrane bound and secreted forms of CD55 have been reported in the literature (Moran et al., 1992).

CD46 (membrane cofactor protein, MCP, see, for example, PCT patent publication No. WO 91/02002) is found on all cells except red blood cells. CD46 binds to C3$b$, and, once bound, promotes the activity of proteases that cleave C3$b$ into inactive fragments, thus preventing C3$b$ accumulation on the cell surface and, in turn, protecting cells from complement attack. Both membrane bound and secreted forms of CD46 have been reported in the literature (Purcell et al., 1991).

CD35 (complement receptor 1, CR1) is a cell surface protein found on a select group of lymphocytes as well as erythrocytes, neutrophils, and eosinophils. Native CR1 causes degradation of C3$b$ molecules adhering to neighboring cells. An active soluble form of CR1 has been produced by recombinant means (see U.S. Pat. No. 5,212,071).

Factor H and C4$b$-binding protein both inhibit alternative C3 convertase activity.

C1 inhibitor is a plasma glycoprotein that inhibits the activity of the C1 component of the classical pathway of complement via inhibition of the proteolytic activities of the C1$r$ and C1$s$ subunits of C1. C1 inhibitor protein migrates in SDS gels at an apparent Mr of 104,000, but has an actual Mr of approximately 76,000. This complement and coagulation inhibitor acts by forming a peptidyl bond with a target proteinase resulting in an inactive complex (see Eldering, 1992).

CIMs of Pathogenic Organisms

Pathogens known to produce CIMs include microbial pathogens such as *Entamoeba histolytica*, which causes amebiasis; *Trypanosoma cruzi*, which causes Chagas' disease; certain strains of group A streptococci; *Salmonella choleraesuis*, various strains of which can produce a number of disease states, including enteric fever and typhoid fever; *Yersinia enterocolitica*, which causes yersiniosis; vaccinia virus; Herpes simplex virus types I and II; and *Herpesvirus saimiri*, which causes disease in monkeys (Braga, et al., 1992; Norris, et al., 1991; Hong, et al., 1990; Heffernan, et al., 1992; Bliska, et al., 1992; Isaacs, et al., 1992; McNearney, et al., 1987; Albrecht and Fleckenstein, 1992; Cooper, 1991; Gooding, 1992; and Rother, et al., 1994). It is likely that other pathogens, including non-microbial pathogens such as worms, produce as yet unidentified CIMs. In addition to those described in general terms above, examples of specific microbial CIMs are reviewed below.

*Herpesvirus saimiri* (HVS), a T-lymphotrophic tumor virus of New World primates, directs the expression of CCPH (complement control protein homolog) and HVS-15 (Rother, et al., 1994), see, for example, copending PCT patent application Ser. No. PCT/US93/00672, filed Jan. 12, 1993, and Albrecht and Fleckenstein, 1992. The structural layout of CCPH is similar to those of CD55 and CD46. CCPH is found as both a membrane glycoprotein (mCCPH) and a secreted derivative (sCCPH). The HVS-15 protein is closely related to the endogenous human CIM, CD59. See, for example, copending PCT patent application Ser. No. PCT/US93/00672, filed Jan. 12, 1993.

The vaccinia virus complement-control protein VCP has been shown to prevent antibody-dependent complement-enhanced neutralization of infectivity and to contribute to viral virulence (Isaacs, et al., 1992).

Herpes simplex virus glycoproteins gC-1 and gC-2 have been shown to inactivate complement component C3$b$, and the presence of either of these glycoproteins in virions has been shown to provide protection against complement-mediated neutralization of viral infectivity (McNearney, et al., 1987).

The M protein of group *A streptococci* is a factor that has been shown to be required for bacterial virulence, and has also been shown to inhibit alternative C3 convertase and classical C5 convertase, two important enzymatic activities needed for the formation of active terminal complement components (Hong, et al., 1990).

The TraT protein of *Escherichia coli* has been shown to be the determinant of the serum resistance conferred by the *E. coli* R factor, which enhances the virulence of this bacterium (Pramoonjago, et al., 1992).

The rck gene of *Salmonella choleraesuis* serotype typhimurium (also known as *Salmonella typhimurium*) has been shown to be the determinant of the serum resistance conferred by the Salmonella virulence plasmid (Heffernan, et al., 1992).

Other CIMs

In addition to these endogenous and microbial CIMs, a number of other proteins are known that can inhibit the complement system.

Cobra venom factor (CoVF or CVF) is a C3$b$-like molecule found in cobra venom that is resistant to C3$b$ inactivating factors (Leventhal, et al., 1993). This C3$b$ analog combines with components of the alternative complement pathway to form a highly stable enzyme complex which exhibits high levels of C3 convertase activity and causes massive consumption of C3, terminal complement components, and other factors. This activity results in the depletion of complement components and the consequent exhaustion of the complement cascade. The end result of CVF action in a body fluid is thus to block terminal complement activity until more complement components make their way into the complement depleted body fluid.

Antibodies reactive with complement components have the potential to block complement component action and thereby to inhibit complement activity. Such complement inhibitory blocking antibodies include the monoclonal antibodies against human C5$b$–9 proteins discussed in U.S. Pat. No. 5,135,916, issued Aug. 4, 1992. In addition to native antibodies, antigen binding fragments (e.g., Fab' preparations) of such immunoglobulins, as well as recombinantly expressed antigen binding proteins, including immunoglobulins, chimeric immunoglobulins, "humanized" immunoglobulins, antigen binding fragments of such immunoglobulins, single chain antibodies, and other recombinant proteins containing antigen binding domains derived from immunoglobulins, all of which can be prepared by methods well known in the art, can be used as CIMs.

Various non-protein CIMs are also known in the art. These include chelation agents such as EDTA, EGTA, and glycosaminoglycans such as heparin, heparin derivatives, and heparan sulfate proteoglycan. Examples of other non-protein CIMs known in the art include:

(1) Rutin poly(H-)sulfate salts and related compounds, see U.S. Pat. No. 4,414,207;

(2) Carboxyalkyl derivatives of rutin poly(H-)sulfate, see U.S. Pat. No. 4,342,753;

(3) Naphthalenetetrayltetrakis(sulfonylimino)-tetrabenzene di- and tricarboxylic acids, see U.S. Pat. No. 4,369,191;

(4) Mono-, di- and tri-adamantylcarbonyl-digalactopyranosyl-glucopyranosyl-fructofuranose sulfate salts, see U.S. Pat. No. 4,359,461;

(5) 6'-(1-Adamantanecarboxylate)-6-O-α-D-galactopyranosyl-α-D-glucopyranose sulfate salts, see U.S. Pat. No. 4,359,460;

(6) O-α-D-Multigalactopyranosyl-O-α-D-multiglucopyranosyl-O-β-D-multifructofuranosyl-glucopyranoside sulfate salts, see U.S. Pat. No. 4,359,459;

(7) O-β-D (and O-α-D) multigalactopyranosyl, xylopyranosyl and glucopyranosyl sulfate salts, see U.S. Pat. No. 4,359,458;

(8) Multi-glucopyranosyl-fructofuranosyl-galactopyranosyl-glucopyranoside sulfate salts, see U.S. Pat. No. 4,357,326;

(9) 5-Phenenyltris (sulfonylimino) tri-benzene mono- and di-sulfonic acids and salts, see U.S. Pat. No. 4,265,908;

(10) Lactobionic acid poly(H-sulfate) and salts thereof, see U.S. Pat. No. 4,258,034;

(11) Modified cyclodextrin sulfate salts, see U.S. Pat. No. 4,247,535;

(12) Ureylene phenylene anionic naphthalenesulfonic acids, see U.S. Pat. No. 4,180,587;

(13) Tri-substituted triazines, see U.S. Pat. No. 4,183,929;

(14) 2,2',2",-[5-phenenyltris(carbonylimino)]tris-2-deoxy-d-glucopyranose and salts thereof, see U.S. Pat. No. 4,120,954;

(15) 2,2',2"-[5-phenenyltris(sulfonylimino)tris]-[2-deoxy-α-D-glucopyranose] dodecakis (H-sulfate) compounds and their salts, see U.S. Pat. No. 4,120,953;

(16) 5-carboxy-phenylenebis(carbonylimino)benzene carboxylic and dicarboxylic acids and salts, see U.S. Pat. No. 4,089,974; and (17) Poly-cation salts of bis (or tris) [4-O-monohexose-oxy]-arylene sulfate derivatives, see U.S. Pat. No. 4,440,758.

SUMMARY OF THE INVENTION

In view of the foregoing state of the art, it is an object of the present invention to facilitate the use of RVVPs to efficiently transduce the cells of a primate patient, e.g., a human patient, upon administration of the RVVPs to cells in contact with the body fluids of the patient.

It is a further object of the invention to provide a means by which retroviral producer cells can be protected from rejection so that they can be effectively implanted into non-immunoprivileged sites in a human patient.

It is an additional object of the present invention to provide pharmaceutical agents for gene therapy in primates, and to provide articles of manufacture containing such agents.

In order to achieve these an other objects, the invention provides methods that consist of administering a complement inhibitor molecule, or a mixture of complement inhibitor molecules, to a body fluid of a patient, either before, at the same time as, or after the administration of RVVPs into the body fluid. The CIMs are administered in order to protect the RVVPs, and/or the producer cells providing the RWPs, from the patient's complement system.

BRIEF DESCRIPTION OF THE DRAWINGS

FIG. 1. RVVP survival in complement deficient sera. LXSN RVVPs were incubated with 40% human serum (Hu Ser), heat-inactivated human serum (HI Hu Ser), or serum deficient in the complement component C1 (C1$d$), C2 (C2$d$), C3 (C3$d$), C5 (C5$d$), C6 (C6$d$), C8 (C8$d$), or C9 (C9$d$). Following pretreatment with serum, the RWPs were titered on NIH/3T3 cells to assess survival. Bars represent the percentage of transducing RVVPs remaining following treatment with serum relative to untreated RVVPs. Data represent a single experiment, one of two so performed.

FIG. 2$a$ Monoclonal antibodies protect chicken erythrocytes from complement-mediated lysis. Monoclonal antibodies specific for the human terminal complement components C5, C6, C8, or C9 were assayed for the ability to protect chicken erythrocytes from hemolysis by human serum complement. Chicken erythrocytes were sensitized with anti-chicken erythrocyte antibody prior to incubation with 10% human serum containing monoclonal antibodies to human terminal complement components (amounts indicated by abscissa). A nonblocking anti-C8 mAb (Anti-C8 NBL) was included as a control. After incubation at 37° C. for 30 minutes, complement activity was determined by measuring disruption of erythrocyte membranes as indicated by hemoglobin release, measured as O.D. at 415 nm. Percent hemolysis relative to a fully lysed control sample was then calculated. Data represent a single experiment, one of two so performed.

FIG. 2$b$ Monoclonal antibodies and CoVF protect RVVPs from complement-mediated inactivation. Monoclonal antibodies specific for the human terminal complement components C5, C6, C7, C8, C9 and cobra venom factor (CoVF) were assayed for the ability to protect RVVPs from human serum complement. Human serum (Hu Ser) was preincubated with functionally blocking mAbs against C5, C6, C7, C8, and C9 and cobra venom factor. LXSN RVVPs preincubated in heat inactivated serum (HI Hu Ser), untreated serum (Hu Ser), serum treated with a nonblocking (NBL) anti-C8 mAb or LXSN RVVPs in the absence of serum were included as positive and negative controls. After pretreatment with serum, the RVVPs were titered on NIH/3T3 cells. Bars indicate the percentage of transducing RVVPs remaining following treatment with serum under the various conditions relative to untreated RVVPs. Data represent a single experiment, one of two so performed.

FIG. 3 RVVP survival in serum or in human whole blood. LXSN RWPs were treated with HBSS, serum, plasma or whole blood in the presence or absence of a functionally blocking anti-C5 mAb and heparin as an anticoagulant. The RVVPs were then titered on NIH/3T3 cells to assess survival. Bars indicate the percentage of transducing RVVPs surviving under the various conditions relative to control treated RVVPs (HBSS). Data represent a single experiment, one of two so performed.

The foregoing drawings, which are incorporated in and constitute part of the specification, illustrate certain embodiments of the invention, and together with the description, serve to explain the principles of the invention. It is to be understood, of course, that both the drawings and the description are explanatory only and are not restrictive of the invention.

DETAILED DESCRIPTION OF THE INVENTION

The present invention relates to gene therapy using retroviral vector particles.

I. RVVPs

General discussions of packaging cells, retroviral vector particles and gene transfer using such particles can be found in various publications including PCT Patent Publication No. WO 92/07943, EPO Patent Publication No. 178,220, U.S. Pat. No. 4,405,712, Gilboa, 1986; Mann, et al., 1983; Cone and Mulligan, 1984; Eglitis, et al., 1988; Miller, et al., 1989; Morgenstern and Land, 1990; Eglitis, 1991; Miller, 1992; Mulligan, 1993, and Ausubel, et al., 1992. The manipulation of retroviral nucleic acids to construct packaging vectors and packaging cells is discussed in, for example, Ausubel, et al., Volume 1, Section III (units 9.10.1–9.14.3), 1992; Sambrook, et al., 1989; Miller, et al., 1989; Eglitis, et al., 1988; U.S. Pat. Nos. 4,650,764, 4,861, 719, 4,980,289, 5,122,767, and 5,124,263; as well as PCT Patent Publications Nos. WO 85/05629, WO 89/07150, WO 90/02797, WO 90/02806, WO 90/13641, WO 92/05266, WO 92/07943, WO 92/14829, and WO 93/14188. To form packaging cells, packaging vectors are introduced into suitable host cells such as those found in, for example, Miller and Buttimore, *Mol. Cell Biol.*, 6:2895–2902, 1986; Markowitz, et al., *J. Virol.*, 62:1120–1124, 1988; Cosset, et al., *J. Virol.*, 64:1070–1078, 1990; U.S. Pat. Nos. 4,650,764, 4,861,719, 4,980,289, 5,122,767, and 5,124,263, and PCT Patent Publications Nos. WO 85/05629, WO 89/07150, WO 90/02797, WO 90/02806, WO 90/13641, WO 92/05266, WO 92/07943, WO 92/14829, and WO 93/14188. Once a packaging cell line has been established, producer cells are generated by introducing retroviral vectors into the packaging cells. Examples of such retroviral vectors are found in, for example, Korman, et al., 1987, *Proc. Natl. Acad. Sci. USA*, 84:2150–2154; Miller and Rosman, *Biotechniques*, 7:980–990, 1989; Morgenstern and Land, 1990; U.S. Pat. Nos. 4,405,712, 4,980,289, and 5,112,767; and PCT Patent Publications Nos. WO 85/05629, WO 90/02797, and WO 92/07943. The retroviral vector includes a psi site and one or more exogenous nucleic acid sequences selected to perform a desired function, e.g., an experimental, diagnostic, or therapeutic function. These exogenous nucleic acid sequences are flanked by LTR sequences which function to direct high efficiency integration of the sequences into the genome of the ultimate target cell.

Many applications of gene therapy using retroviral vector particles (RWPs) are known and have been extensively reviewed (see, for example, Boggs, 1990; Kohn, et al., 1989; Lehn, 1990, Verma, 1990; Weatherall, 1991; and Felgner and Rhodes, 1991).

A variety of genes and DNA fragments can be incorporated into RVVPs for use in gene therapy. These DNA fragments and genes may encode RNA and/or protein molecules which render them useful as therapeutic agents. Protein encoding genes of use in gene therapy include those encoding various hormones, growth factors, enzymes, lymphokines, cytokines, receptors, and the like.

Among the genes which can be transferred are those encoding polypeptides that are absent, are produced in diminished quantities, or are produced in mutant form in individuals suffering from a genetic disease. Other genes of interest are those that encode proteins that, when expressed by a cell, can adapt the cell to grow under conditions where the unmodified cell would be unable to survive, or would become infected by a pathogen. Genes encoding proteins that have been engineered to circumvent a metabolic defect are also suitable for transfer into the cells of a patient. Such genes include the transmembrane form of CD59 discussed in copending U.S. patent application Ser. No. 08/205,720, filed Mar. 3, 1994, entitled "Terminal Complement Inhibitor Fusion Genes and Proteins" and copending U.S. patent application Ser. No. 08/206,189, filed Mar. 3, 1994, entitled "Method for the Treatment of Paroxysmal Nocturnal Hemoglobinuria".

In addition to protein-encoding genes, RVVPs can be used to introduce nucleic acid sequences encoding medically useful RNA molecules into cells. Examples of such RNA molecules include anti-sense molecules and catalytic molecules, such as ribozymes.

In order to expedite rapid transduction by eliminating the need to wait for target cells to divide, and to allow transduction of cells that divide slowly or not at all, the use of RVVPs that can transduce non-dividing cells may be preferred. Such RVVPs are disclosed in copending U.S. patent applications Ser. Nos. 08/181,335 and 08/182,612, both entitled "Retroviral Vector Particles for Transducing Non-Proliferating Cells" and both filed Jan. 14, 1994. These patent applications also discuss specific procedures suitable for producing packaging vectors and retroviral vectors as well as the use of such vectors to produce packaging cells and producer cells, respectively.

II. Protection of RVVPS from Complement Attack

The present invention provides new approaches for the administration of RVVPs to the body fluids of a patient. Significantly, the present invention allows for the use of more practical protocols for RVVP administration. It does so by eliminating the need to remove the target cells from body fluids prior to administration of the RVVPs. Specifically, in accordance with the invention, CIMs and RVVPs are administered to cells while those cells are in contact with body fluids such as blood, plasma, serum, lymph, the fluids making up bone marrow, and the like.

A variety of CIMs can be used to protect RVVPs from complement attack. Those CIMs include the molecules discussed above under the heading "Inhibitors of the Complement System." Preferred CIMs are sCCPH, anti-complement component mAbs, and heparin (particularly, heparin derivatives with reduced anticoagulant activity).

Heparin is commonly used as an antithrombotic agent and to decoagulate blood. In addition to its anticoagulant and antithrombotic functions, heparin interferes with the activities of various complement components and cofactors, including the interactions of C1, C2, and C4 during the formation of classical pathway C3 convertase, and the assembly of the C5$b$–9 complex. Heparin is thus considered to be a complement inhibitor. In clinical use, heparin is generally administered at doses resulting in levels in body fluids (e.g., blood or bone marrow aspirates) of less than 20 units per ml. Such levels provide less than a 50% inhibition of the hemolytic titer of the body fluid. As used in the practice of the present invention, heparin (or a heparin derivative) is administered in an amount sufficient to inhibit the hemolytic titer of the body fluid to which it is administered by at least 50%.

Various derivatives of heparin are known in the art that possess reduced anticoagulant and antithrombotic activity while maintaining complement inhibitor activity. These include those described in Ishihara et al., 1993, J. Biol. Chem. 268:4675–4683; Weiler et al., 1992, J. Immunol. 148:3210–3215; and Maillet et al., 1988, Molec. Immuno. 25:917–923.

The CIMs can be used to protect a variety of RVVPs. Preferred RVVPs are those suitable for gene therapy, including the LXSN particles discussed below in the examples. As discussed above, such RVVPs will include a gene or other nucleic acid sequence whose transfer is desired.

In accordance with the present invention, CIMs are administered to target cells via administration to the body fluids of a patient. The CIMs can be used to protect RVVPs in a variety of ways. As discussed above, most gene therapy protocols involve treating target cells from the patient ex vivo and then reintroducing the cells into the patient. In these protocols, the target cells are typically washed to remove body fluids, RVVPs are added in a suitable buffer, and the cells are incubated with the RVVPs. In accordance with the present invention, the RVVPs are normally administered to the target cells while the cells are bathed in at least some body fluids, e.g., as a result of incomplete washing.

The CIMs can be administered either before, during, or after the administration of the RWPs to the target cells, although the addition of the CIMs after the administration of the RVVPs is not preferred.

In accordance with the invention, RVVPs may be administered to the target cells via administration to the body fluids bathing cells in the ex vivo unwashed state using otherwise conventional protocols for ex vivo transduction of target cells, or may be administered to body fluids in vivo. In such in vivo applications, the injection of RVVPs directly into solid tissues is considered to be administration to body fluids, as the cells in solid tissues are bathed in interstitial fluids, and the RWPs enter the target cells following mixture with such fluids. In accordance with the invention, the administration of an amount of a CIM (or of a mixture of CIMs) sufficient to reduce the hemolytic titer of a body fluid by at least 50% is sufficient to provide a useful reduction of the inactivation of RVVPs by the complement system when the particles are administered to the body fluids of a patient.

In in vivo applications where the RVVPs are administered by injection into a solid tissue, the CIMs are typically delivered to the interstitial fluids surrounding the target cells by systemic routes, e.g., by co-injection with the RWPs or by separate intravenous injection. In such cases, the hemolytic titer of the patient's blood, plasma, or serum provides a convenient measure for determining dosage of the CIM. Preferably, the CIM is administered only once during each RVVP treatment. In some gene therapy protocols, multiple rounds of RVVP administration may be used. In such cases, the administration of CIMs is repeated in conjunction with each administration of RVVPs. Whether administered in vivo or ex vivo, RVVPs are generally administered between about $10^6$ and $10^{14}$ colony forming units per patient per treatment. Similar approaches are followed when producer cells, as opposed to isolated RVVPs, are administered, e.g., implanted (see below).

In certain cases, gene therapy may be carried out by a procedure in which a retroviral producer cell (i.e., an engineered cell producing RVVPs) is implanted into the body of the patient to be treated. This may be a particularly desirable procedure in the treatment of certain cancers. Recent in vivo studies have demonstrated that procedures involving the implantation of producer cells into rat solid tumors can effectively deliver RVVPs to adjacent cells (Culver et al., 1992). In one variation of such procedures, producer cells are engineered to express the herpes simplex virus thymidine kinase (HSVTK) gene. Treatment of a patient with ganciclovir post-implantation will kill the HSVTK expressing producer cells as well as any immediately surrounding cells, which, in such procedures, will be tumor cells.

In related studies, producer cells injected into the brain of rats or monkeys were shown to survive for approximately 15 days without proliferating (Ram et al., 1993). The survival of xenogeneic producer cells in the primate brain is not surprising considering that the brain is an immunoprivileged site relative to complement activity (Widner and Brundin, 1988) and therefore, hyperacute rejection (HAR) commonly associated with xenotransplants into primates is less likely to occur in the brain. HAR of xenografts in primates normally occurs within minutes of transplantation due to the activation of the classical complement pathway by preexisting antibodies to alpha-galactosyl epitopes found on the surface of mammalian cells excluding man, apes and Old World monkeys (Galili et al., 1987; and Neethling et al., 1994).

Transient inactivation of the complement cascade in accordance with the methods of the present invention will, in addition to protecting RVVPs, temporarily prevent hyperacute rejection of xenogeneic retroviral producer cells implanted in non-immunoprivileged sites, allowing the producer cells to survive until complement activity rebounds or until the producer cells are eliminated through the actions of the cellular immune system. Concomitantly, in accordance with the invention, the RVVPs liberated from the producer cells will be protected from inactivation.

Although producer cells and RVVPs (in the absence of replication competent virus) have not been shown to be toxic or pathologic in primates, transient inactivation of complement in accordance with the present invention provides an additional safety mechanism for the use of implanted producer cells to effect gene therapy; when complement inhibition ceases, producer cells and RVVPs will be eliminated.

In accordance with the invention, the administration of an amount of a CIM (or of a mixture of CIMs) sufficient to reduce the hemolytic titer of the body fluid by at least 50% is sufficient to provide a useful reduction of the inactivation of RVVPs by the complement system when the particles are administered to the body fluids of a patient.

III. Pharmaceutical Compositions

The CIMs used in the methods of the invention can be formulated as pharmaceutical compositions. Such compositions will generally include a pharmaceutically effective carrier, such as saline, buffered phosphate buffered) saline, Hank's balanced salts solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. See, for example, *Remington's Pharmaceutical Sciences,* Mack Publishing Company, Philadelphia, Pa., 17th ed., 1985. In addition to the CIMs, the formulations may also contain therapeutic RVVPs or producer cells or both.

The formulations of the invention may be used to facilitate the in vivo administration of retroviral vector particles to a patient. In connection with such in vivo administration, the retroviral vector particles can be modified by various genetic modifications of the cells from which the producer cells producing the RVVPs are derived. These modifications include those made in accordance with the procedures discussed in copending U.S. patent application Ser. No. 08/278,630, entitled "Retroviral Vector Particles Expressing Complement Inhibitor Activity", which is being filed concurrently herewith in the names of James M. Mason and Stephen P. Squinto. These modifications also include those made in accordance with the procedures discussed in copending U.S. patent application Ser. No. 08/278,282, entitled "Methods for Reducing Hyperacute Rejection of Xenografts", which is being filed concurrently herewith in the names of Mauro S. Sandrin, William L. Fodor, Russell P. Rother, Stephen P. Squinto, and Ian F. C. McKenzie, and in copending U.S. patent application Ser. No. 08/278,639, entitled "Retroviral Transduction of Cells in the Presence of Complement", which is being filed concurrently herewith in the names of Russell P. Rother, Scott A. Rollins, William L. Fodor, and Stephen P. Squinto, now abandoned. In addition, RVVPs used in the methods of the invention may be treated in accordance with the procedures discussed in co-pending application Ser. No. 08/098,944, filed Jul. 28, 1993, in the name of James M. Mason and entitled "Pre-binding of Retroviral Vector Particles with Complement Components to Enable The Performance of Human Gene Therapy In Vivo." Further, the RVVPs and/or producer cells used in the methods of the invention can be administered in combination with the compositions of copending U.S. patent application Ser. No. 08/278,639, entitled "Retroviral Transduction of Cells in the Presence of Complement", which is being filed concurrently herewith in the names of Russell P. Rother, Scott A. Rollins, William L. Fodor, and Stephen P. Squinto, now abandoned.

Such CIMs or CIM/RVVP combinations or CIM/producer cell combinations or CIM/RVVP/producer cell combinations can be administered by various methods known in the art. The administration can be performed locally, e.g., by aerosol, transmucosal, or transdermal delivery, or, more typically, by a systemic route, e.g., orally, intravenously, intraperitoneally, intramuscularly, transdermally, intradermally, subdermally, transmucosally, or intrathecally. For systemic administration, injection is generally preferred.

The pharmaceutical compositions of the invention are suitable for use in a variety of drug delivery systems. Langer, *Science*, 249:1527–1533, 1990, reviews various drug delivery methods currently in use. In some cases, the drug delivery system will be designed to optimize the biodistribution and/or pharmacokinetics of the delivery of the retroviral vector particles. See, for example, *Remington's Pharmaceutical Sciences, supra,* Chapters 37–39. For example, the particles can be incorporated in vesicles composed of substances such as proteins, lipids (for example, liposomes), carbohydrates, or synthetic polymers. See, for example, Langer, 1990, supra.

In certain preferred embodiments, the invention also provides articles of manufacture consisting of pharmaceutical compositions that contain CIMs and packaging material indicating that the pharmaceutical composition is to be used in conjunction with the administration of RWPs and/or producer cells.

In further preferred embodiments, the invention provides articles of manufacture consisting of (1) pharmaceutical compositions that contain (a) CIMs and (b) RVVPs and/or producer cells, and (2) packaging material indicating that the pharmaceutical composition is to be used to effect gene therapy.

The pharmaceutical compositions of the invention can be administered in a variety of unit dosage forms. The dose will vary according to, e.g., the particular CIM, RVVP, or producer cell, the manner of administration, the particular disease being treated and its severity, the overall health and condition and age of the patient, and the judgment of the prescribing physician. Dosage levels of RVVPs for human subjects are generally between about $10^6$ and $10^{14}$ colony forming units of retroviral vector particles per patient per treatment. Producer cells are administered in sufficient numbers to produce therapeutic levels of RVVPs, e.g. at least about $10^3$–$10^4$ producer cells. Dosage levels of CIMs are adjusted so that the CIMs provide an at least 50% reduction of the hemolytic titer of the body fluid to which the RWPs are administered.

In terms of clinical practice, the methods of the present invention will have broad therapeutic utility in facilitating the treatment of a wide range of inherited and acquired diseases and medical conditions including, without limitation, hematologic diseases, cardiopulmonary diseases, endocrinological diseases, immunological diseases, neoplasias, and the like.

Without intending to limit it in any manner, the present invention will be more fully described by the following examples.

MATERIALS AND METHODS

Virus preparation and virus titering assay.

High titer amphotropic RVVP stocks of the retroviral vector LXSN ($1\times10^6$ CFUs/ml) used in the following examples were prepared and assayed as follows: Amphotropic RVVP were produced through an intermediate ecotropic packaging cell line as described in Warren, et al., 1987. Briefly, psi 2 cells (obtained from Dr. Stephen L. Warren, Department of Pathology, Yale University School of Medicine, New Haven, Conn.) were transfected with pLXSN (Miller et al., 1989) using DMSO shock followed by selection in DMEM containing 500 µg/ml (active) G418 and 10% heat inactivated FCS.

Transfectants were pooled and a 24 hour supernatant was harvested from the cells at 90% confluency. The ecotropic RVVP stock was used to infect the amphotropic packaging cell line PA317 (ATCC designation CRL 9078). These cells were also selected in the same medium with G418, following which an RVVP stock was collected from pooled transductants in the same medium without G418.

Serial dilutions of RVVP samples were assayed for titer of infectious RVVP particles on NIH/3T3 cells (ATCC designation CCL 163). $2.5\times10^4$ cells were plated in 2 ml of DMEM containing 10% FBS (referred to hereinafter as D10) in wells of 6-well plates. The following day, medium in each well was replaced with 2 ml of D10 containing 8 mg/ml of polybrene. The RVVP sample was then added. Ten-fold or 100-fold serial dilutions were made from the original well and added to adjacent wells. The plates were then incubated for 24 hours. Medium was then once again replaced with 2 ml of the D10, in this case containing 500 mg/ml of G418 (active).

Selection was accomplished by incubation in the G418 containing D10 for 10 days with 2 changes of medium during this period. Following this selection, medium was removed and surviving colonies were fixed and stained for 15 minutes with a saturated solution of methylene blue in methanol followed by a brief rinse with water.

Hemolytic assay

The complement activity of whole human blood was assayed by conventional hemolytic assays. Chicken erythrocytes (Lampire Biological, Pipersville, Pa.) were washed 4× in GVBS$^{++}$ (Sigma Chemical Company, St. Louis, Mo.) and sensitized with anti-chicken erythrocyte IgG (Inter-cell Technologies, Hopewell, N.J.) by adding 0.1% Ab to GVBS$^{++}$ containing $5\times10^7$ cells/ml for a 15 minute incubation at 4° C. Cells were washed 2× and resuspended in GVBS$^{++}$ at a concentration of $1\times10^8$ cells/ml.

The sensitized chicken erythrocytes (30 µl) were added to plasma (100 µl final volume after dilution with HBSS of GVBS$^{++}$) for a 30 minute incubation at 37° C. in a 96 well plate. The plate was then centrifuged at 10,000× g for 2 minutes and the absorbance of each supernatant was measured as O.D. at 415 nm.

Figure 3:
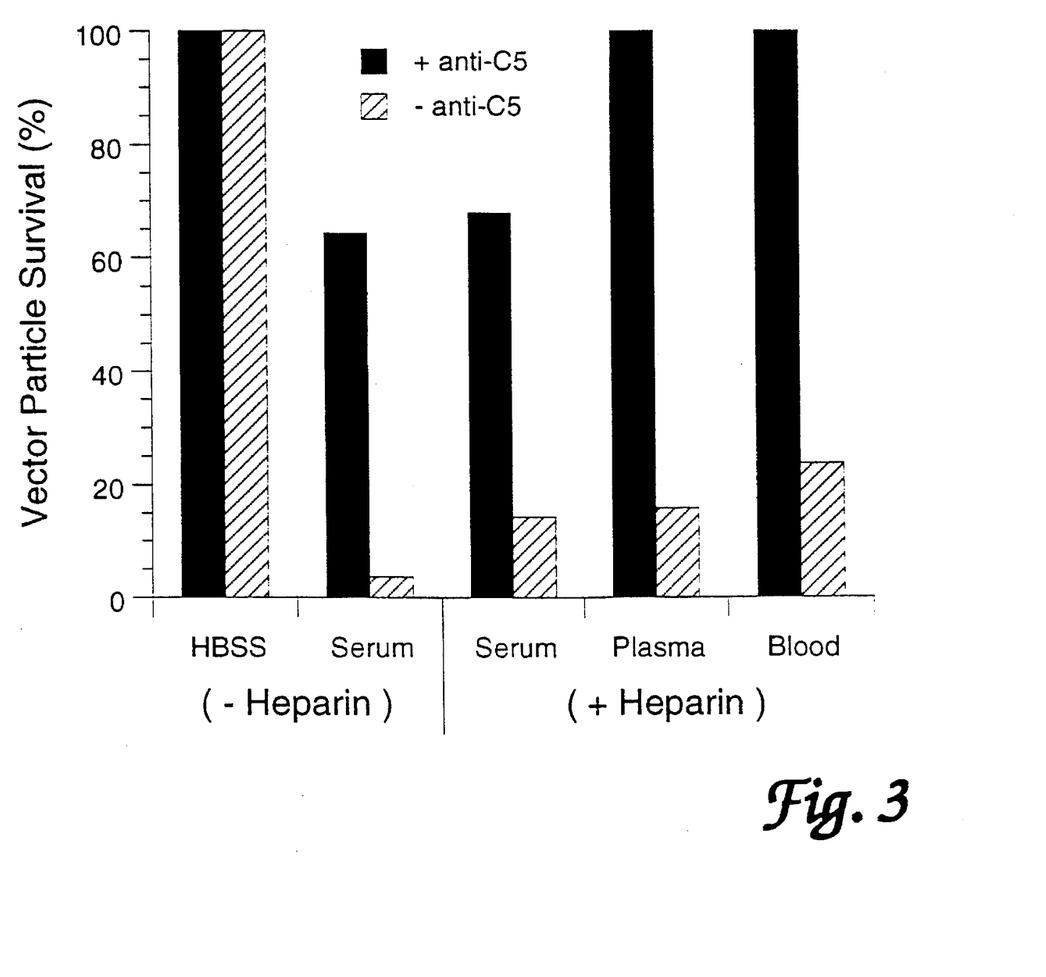
Figure 4:
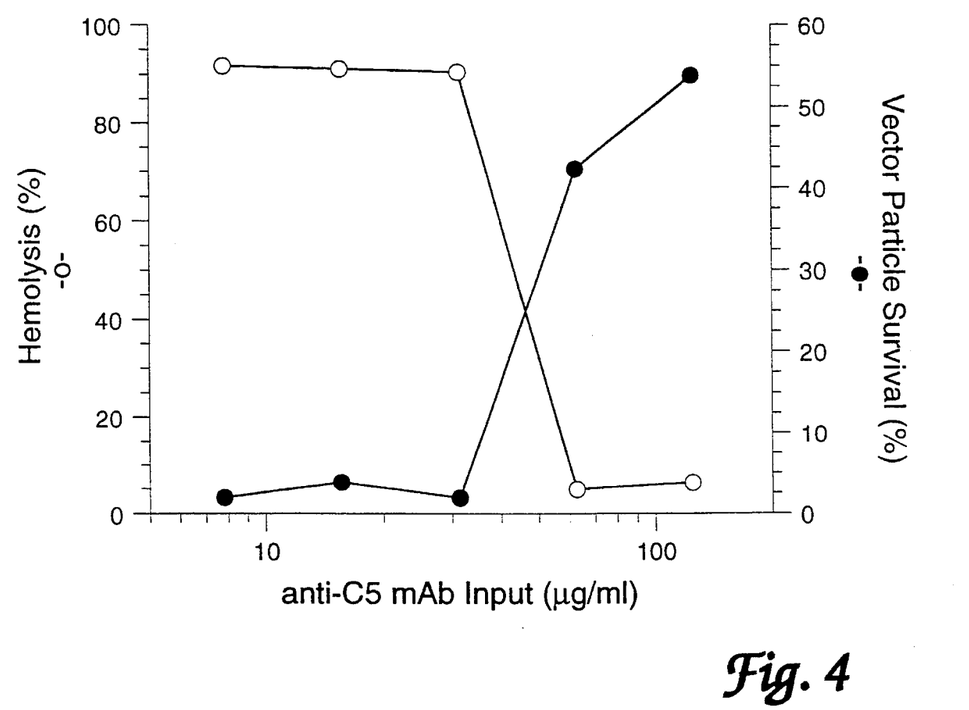
FIG. 4 Correlation between complement activity and vector particle survival. To correlate levels of complement activity with vector particle survival, 40% human serum was incubated in the presence of various concentrations of anti-C5 mAb N19/8 and the residual complement activity was determined as hemolytic titer in an erythrocyte hemolytic assay. PA317-LXSN vector particle survival was simultaneously assessed by preincubating vector particles with aliquots of the anti-C5 mAb treated sera before titering on NIH/3T3 cells.

In the experiments presented in FIGS. 3 and 4 heparinized whole human blood (50 U heparin/ml blood) was incubated with various concentrations of monoclonal antibody N19/8 for 30 min at 37° C. N19/8 is a functionally blocking anti-C5 mAb raised against human C5. The blood was then centrifuged at 15,000× g for 10 minutes and the plasma was recovered. Blood preincubated with anti-mouse-C5 mAb BB5.1 (Frei, et al., 1987), obtained from Dr. Brigitta Stockinger of the National Institute for Medical Research, Mill Hill, London, England, was used as a negative control. This mAb blocks mouse C5, but not human C5.

Viral killing assays in human serum

RVVP samples were preincubated (pretreated) with human sera and then titered on 3T3 cells to assess viral survival as described above. In each case, a 20 µl sample of the LXSN viral supernatant ($1\times10^3$ CFUs/ml) was mixed with 80 ml of pre-diluted human serum (Sigma Chemical Co., St. Louis, Mo.) or 80 µl of a pre-diluted sample of complement deficient human serum, to yield a 100 µl reaction mixture. This reaction mixture was then incubated for 30 minutes at 37° C. Complement deficient human sera used in these experiments included C1 deficient serum (C1d), C2 deficient serum (C2d), C3 deficient serum (C3d), C5 deficient serum (C5d), C6 deficient serum (C6d), C8 deficient serum (C8d), and C9 deficient serum (C9d) (all from Quidel Corporation, San Diego, Calif.). Each pretreatment was carried out with the serum at a final concentration of 40%, which was achieved by pre-dilution with buffer. Pretreated RVVP samples were ritered by adding the RVVP/serum mixtures to NIH/3T3 cells in 2 ml of D10 as described above. RVVP samples pretreated with heat inactivated serum, and virus samples pretreated with buffer alone, served as controls. In certain experiments other controls were used, as described below. Percent survival under the different conditions was calculated relative to survival of RVVPs incubated with buffer alone.

In the experiments characterizing the blockade of complement-mediated inactivation of RVVPs, serum was preincubated with the complement inhibitory reagent being characterized for 30 min at 37° C. prior to the addition of the RVVP sample. An additional control in these experiments was a non-blocking (not complement inhibitory) anti-C8 mAb (Catalog #A249, Quidel Corporation, San Diego, Calif.) Complement inhibitory reagents included anti-C5 mAb at 250 mg/ml (N19/8, Wurzner, et al., 1991, Otto Goetze, University of Gottingen, Gottingen, Germany), anti-C6 mAb at 500 mg/ml (WU6-4, Wurzner, et al., 1991, Otto Goetze, University of Gottingen, Gottingen, Germany), anti-C8 mAb at 500 mg/ml (133.3, Peter Sims, Blood Research Institute, Milwaukee, Wis.), anti-C9 mAb at 750 mg/ml (135.3, Peter Sims, Blood Research Institute, Milwaukee, Wis.), and cobra venom factor (Quidel Corporation) at 35 units per 100 µl reaction mixture.

Viral killing assay in human whole blood and plasma

Viral stocks were exposed to fresh human blood, plasma (40%) or serum (40%) previously incubated in the presence or absence of the N19/8 anti-C5 mAb and subsequently titered on NIH/3T3 cells. More specifically, 500 µl of HBSS diluted blood, plasma or serum was incubated with 180 µl of either N19/8 (1 mg/ml) or HBSS (Hank's balances salt solution, Sigma) for 30 min at 37° C. with shaking. Seven microliters of LXSN viral stock (1×10$^6$ CFUs/ml) was then added to each sample followed by an additional 37° C. incubation for 2 hours. All samples were centrifuged at 3000× g for 15 min and 250 µl of each supernatant was added to 3T3 cells in 2 ml of D10 for titering as described above.

EXAMPLES

Example 1: Inactivation of LXSN retroviral vector particles in human serum.

Figure 1:
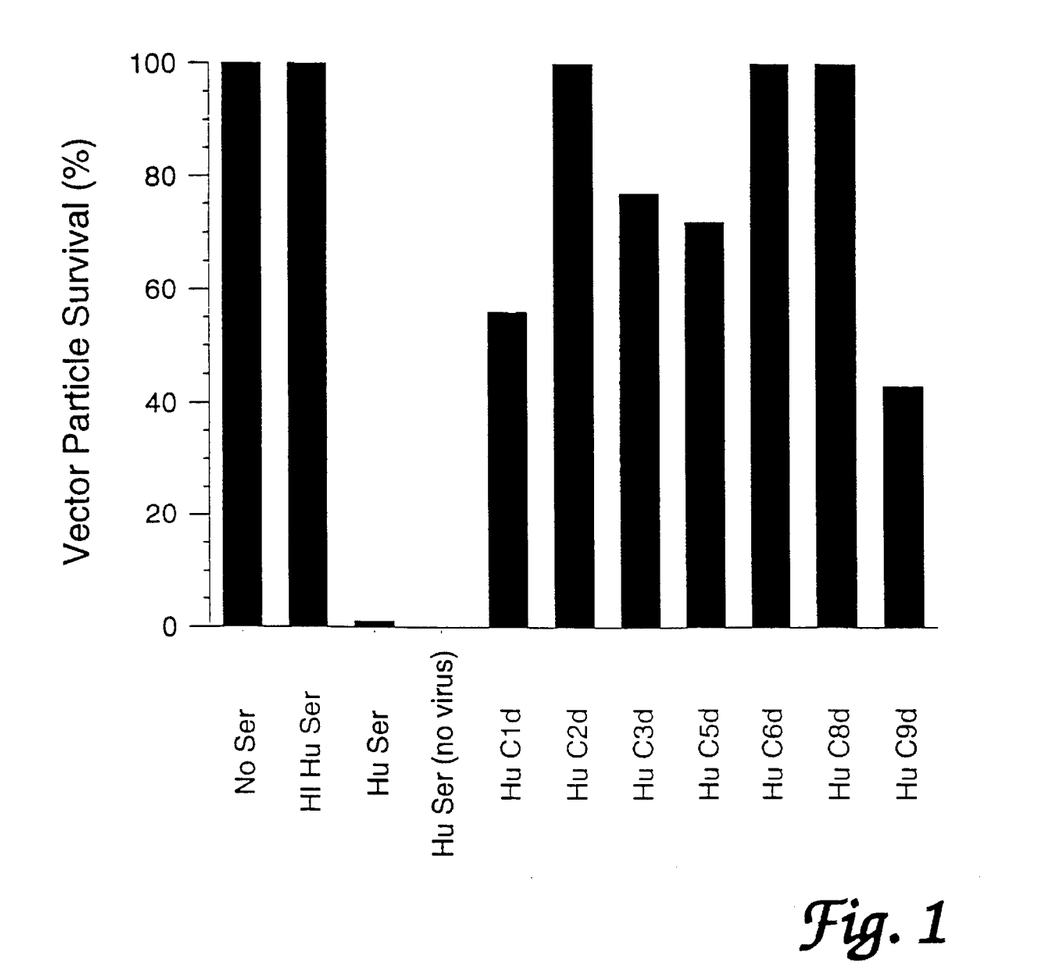

Previous studies have demonstrated that many types of retroviruses are lysed by human or nonhuman primate sera (Welsh et al., 1975; Welsh et al., 1976; Cooper et al., 1976; and Bartholomew et al., 1978). Particles of the Moloney murine leukemia virus derived vector LXSN were subjected to treatment as follows. RVVPs were treated with either complete human serum or sera made deficient in various components of the complement cascade. The activity of the RVVPs in transducing NIH/3T3 cells was then determined. Percent survival was calculated relative to particles incubated in the absence of serum. Preincubation of LXSN with 40% human serum (the effective concentration of serum in whole human blood) totally inactivated the RVVPs, while heat inactivated serum had no effect on RVVP titer (FIG. 1). In contrast, human serum deficient in C1, C2, C3, C5, C6, C8 or C9 did not totally inactivate the RVVPs, with the percentage of surviving RVVPs ranging from 40% to 100%. Differences in the amount of inactivation of the RVVPs by each deficient serum is believed to reflect incomplete depletion of the particular complement component. These data confirm the ability of human serum to effectively inactivate LXSN and demonstrate that this process can be inhibited at various points in the complement cascade. Furthermore, deposition of complement components short of a functional MAC does not appear to interfere with the ability of the RVVP to bind and enter the cell.

Example 2: Protection of LXSN from complement-mediated inactivation by CIMs.

Figure 2A:
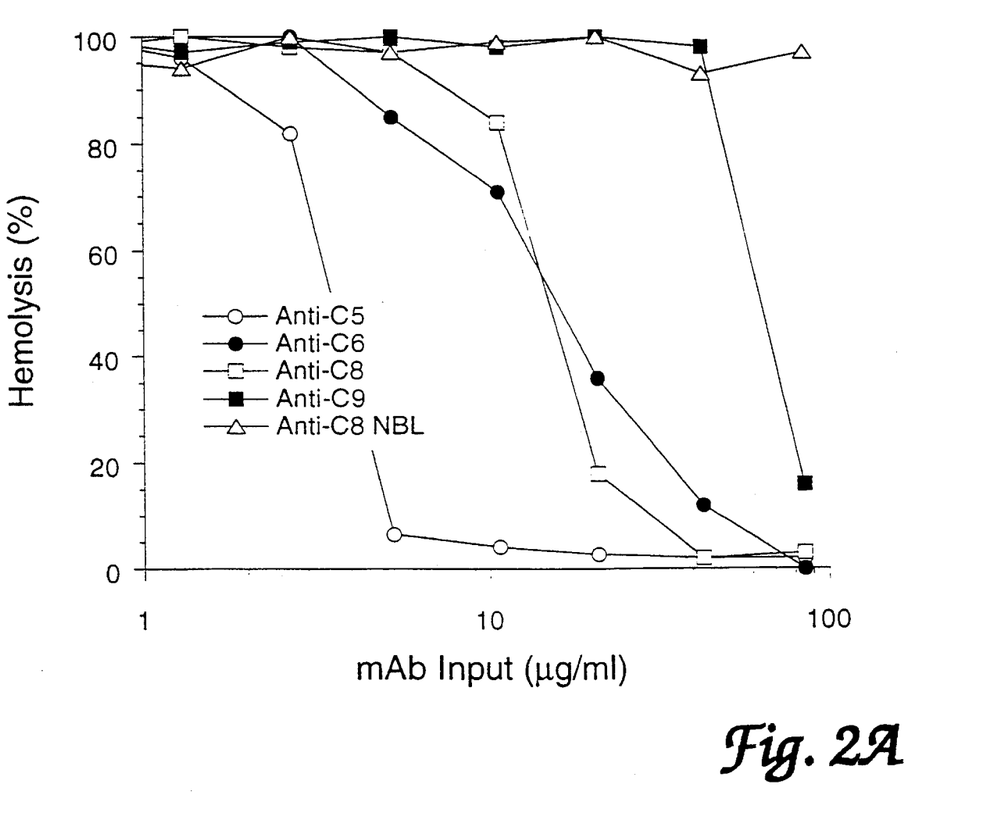

Functionally blocking mouse mAbs raised against human C5, C6, C7, C8 or C9 were incubated with human serum prior to the addition of RVVPs. FIG. 2A confirms that such antibodies are effective in preventing hemolysis of chicken erythrocytes.

Figure 2B:
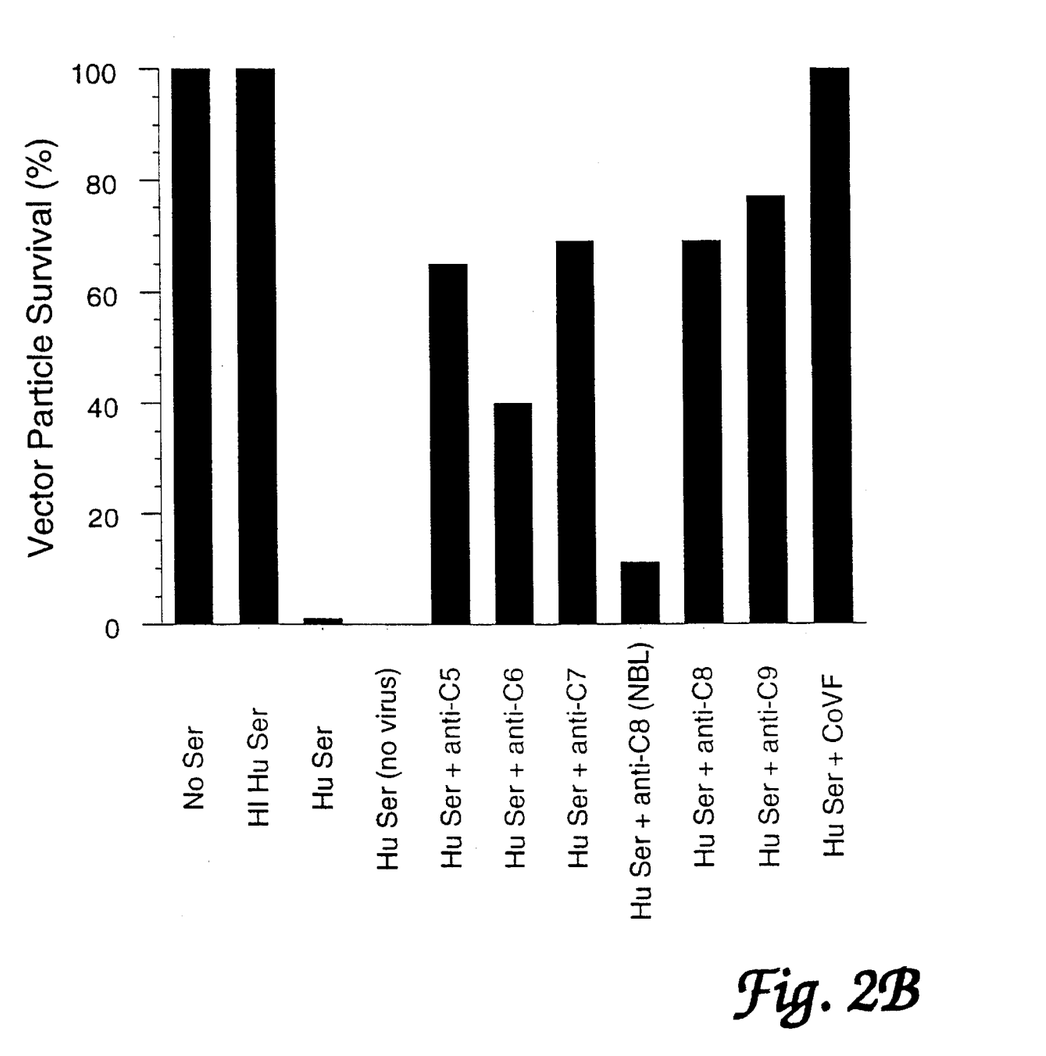

All blocking antibodies successfully inhibited RVVP inactivation (FIG. 2B). Additionally, cobra venom factor (CoVF), which exhausts terminal complement components, totally prevented the inactivation of RVVPs. In contrast, a nonblocking anti-C8 mAb had very little effect on inhibiting RVVP inactivation. These results indicate that functionally blocking anti-complement antibodies or CoVF are effective reagents in preventing complement-mediated destruction of LXSN.

Example 3: LXSN survival in whole human blood.

The survival of LXSN in whole human blood or plasma in the presence or absence of N19/8 anti-C5 mAb was determined. As shown in FIG. 3, LXSN was completely inactivated in serum in the absence of N19/8 anti-C5 mAb, while pretreatment of serum with the antibody effectively protected the virus from inactivation in serum (FIGS. 2B, 3, and 4). Furthermore, the N19/8 anti-C5 mAb dramatically increased the ability of LXSN to survive in whole human blood or plasma (FIG. 3). Control preincubation of the virus with HBSS had no effect on viral titer (FIG. 3).

Example 4: Anti-C5 mAb-mediated depletion of complement in human serum.

The N19/8 anti-C5 mAb was added at different concentrations to 40% human serum which was subsequently assayed for complement activity on chicken erythrocytes. The functionally blocking anti-C5 mAb N19/8 completely inhibited the complement activity of human serum at a concentration of about 60 µg/ml. Considering that the average concentration of C5 in human serum is 70 µg/ml (Male, 1986), which is roughly equivalent to 30 µg/ml in whole human blood, and that the C5 molecule and the antibody molecule are roughly the same size, the N19/8 anti-C5 mAb inhibited C5 at an approximately 2:1 molar ratio.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

REFERENCES

Albrecht and Fleckenstein, 1992. *J Virology* 66(6), pp. 3937–3940.

Anderson, 1992. *Science* 256, pp. 808–813.

Ausubel et al., 1992. *Current Protocols in Molecular Biology*, Wiley Interscience, John Wiley and Sons, N.Y. Volume 1, Section III, units 9.10.1–9.14.3.

Bartholomew et al., 1978. *J Exp Med* 147, pp. 844–853.

Bartholomew et al., 1980. *Biochemistry* 19, pp. 2847–2853.

Bliska et al., 1992. *Proc Natl Acad Sci, USA* 89, pp. 3561–3565.

Boggs, 1990. *Int J Cell Cloning* 8, pp. 80–96.

Braga et al., 1992. *J Clin Invest.* 90, pp. 1131–1137.

Cone and Mulligan, 1984. *Proc Natl Acad Scif, USA* 81, pp. 6349–6353.

Cooper et al., 1976. *J Exp Med* 144, pp. 970–984.

Cooper, 1991. *Immunol Today* 12, pp. 327–331.

Cosset et al., 1990. *J Virol* 64, pp. 1070–1078.

Culver et al., 1992. *Science* 256, pp. 1550–1552.

Eglitis et al., 1988. *Biotechniques* 6, pp. 608–614.

Eglitis, 1991. *Human Gene Therapy* 2, 195–201.

Eldering, 1992. *J Biol Chem* 263, pp. 11776–11779.

Felgner and Rhodes, 1991. *Nature* 349, pp. 351–352.

Frei et al., 1987. *Mol Cellular Probes* 1, pp. 141–149.

Galili et al., 1987. *Proc Natl Acad Sci, USA* 84, pp. 1369–1373.

Gilboa, 1986. *Biotechniques* 4, pp. 504–512.

Gooding, 1992. *Cell* 71, pp. 5–7.

Heffernan et al., 1992. *J Bacteriol* 174, pp. 84–91.

Hong et al., 1990. *Infect and Immunol* 58, pp. 2535–2541.

Isaacs et al., 1992. *Proc. Natl Acad Sci, USA* 89, pp. 628–632.

Ishihara et al., 1993. *J Biol Chem* 268, pp. 4675–4683.

Kohn et al., 1989. *Cancer Invest* 7, pp. 179–192.

Korman et al., 1987. *Proc Natl Acad Sci, USA* 84, pp. 2150–2154.

Langer, 1990. *Science* 249, pp. 1527–1533.

Lehn, 1990. *Bone Marrow Transplantation* 5, pp. 287–293.

Lehto and Meri, 1993. *J Immunology* 151, pp. 4941–4949.

Leventhal et al., 1993. *Transplantation* 55, pp. 857–866.

Maillet et al., 1988. *Molec Immuno* 25, pp. 917–923.

Male, 1986. *Immunology: An Illustrated Outline.* Gower Medical Publishing Ltd., London, England, pp. 84.

Mann et al., 1983. *Cell.* 33, pp. 153–159.

Markowitz et al., 1988. *J Virol* 62, pp. 1120–1124.

McNearney et al., 1987. *J Exp Med* 166, pp. 1525–1535.

Miller and Buttimore, 1986. *Mol Cell Biol* 6, pp. 2895–2902.

Miller and Rosman, 1989. *Biotechniques* 7, pp. 980–990.

Miller et al., 1989. *Biotechniques* 7, pp. 981–990.

Miller, 1992. *Nature* 357, pp. 455–460.

Moran et al., 1992. *J Immunol* 140, pp. 1736–1743.

Morgenstern and Land, 1990. *Nucleic Acids Res* 18, pp. 3587–3596.

Mulligan, 1983. In *Experimental Manipulation of Gene Expression* Inouye (ed), pp. 155–173.

Mulligan, 1993. *Science* 260, pp. 926–932.

Neethling et al., 1994. *Transplantation* 57, pp. 959–963.

Norris et al., 1991. *J Immunol* 147, pp. 2240–2247.

Pramoonjago et al., 1992. *J Immunol* 148, pp. 827–836.

Purcell et al., 1991. *Immunogenetics* 33, pp. 335–344.

Ram et al., 1993. *J Neurosurg* 79, pp. 400–407.

*Remington's Pharmaceutical Sciences,* Mack Publishing Company, Philadelphia, Pa., 17th ed., 1985.

Roitt et al., 1988. *Essential Immunology,* 6th Ed. Backwell Scientific Publications, Oxford, England.

Rooney and Morgan, 1992. *Immunology* 76, pp. 541–547.

Rother et al., 1994. *J Virology* 68(2), pp. 730–737.

Sambrook et al., 1989. *Molecular Cloning—A Laboratory Manual, 2nd Ed.* Cold Spring Harbor Laboratory, Cold Spring Harbor, N.Y.

Tschopp et al., 1988. *Biochemistry* 27, pp. 4103–4109.

Verma, 1990. *Scientific American* 263(5), pp. 68–84.

Warren et al., 1987. *Mol Cell Bio* 7, pp. 1326–1332.

Weatherall, 1991. *Nature* 349, pp. 275–276.

Weiler et al., 1992. *J Immunol* 148, pp. 3210–3215.

Welsh et al., 1975. *Nature* 257, pp. 612–614.

Welsh et al., 1976. *Virology* 74, pp. 432–440.

Widner and Brundin, 1988. *Brain Research Reviews* 13, pp. 287–324.

Wurzner et al., 1991. *Complement Inflammation* 8, pp. 328–340.

What is claimed is:

1. A method for protecting retroviral vector particles from inactivation by a human or Old World primate body fluid comprising administering at least one soluble complement inhibitor molecule to the body fluid in an amount sufficient to reduce the hemolytic titer of the body fluid by at least 50%.

2. The method of claim 1 wherein the body fluid is a heparin decoagulated bone marrow aspirate diluted in tissue culture medium.

3. The method of claim 1 wherein the body fluid is selected from the group consisting of blood, plasma, or serum.

4. The method of claim 1 in which the at least one soluble complement inhibitor is a complement inhibitory anti-complement component antibody.

5. The method of claim 4 wherein the anticomplement component antibody is a complement inhibitory anti-C5 monoclonal antibody.

* * * * *